(12) United States Patent
Meyer et al.

(10) Patent No.: US 11,273,118 B2
(45) Date of Patent: Mar. 15, 2022

(54) COMPOSITIONS AND METHODS FOR IMPROVING SKIN QUALITY

(71) Applicant: ZIM BIOSCIENCES, INC., Solana Beach, CA (US)

(72) Inventors: Jane M. Meyer, Carlsbad, CA (US); Nikita Malavia, San Diego, CA (US); Stephen Alexander Charles, Los Altos, CA (US)

(73) Assignee: Zim Biosciences, Inc., Solana Beach, CA (US)

( * ) Notice: Subject to any disclaimer, the term of this patent is extended or adjusted under 35 U.S.C. 154(b) by 0 days.

(21) Appl. No.: 15/315,795

(22) PCT Filed: Jun. 4, 2015

(86) PCT No.: PCT/US2015/034199
§ 371 (c)(1),
(2) Date: Dec. 2, 2016

(87) PCT Pub. No.: WO2015/187951
PCT Pub. Date: Dec. 10, 2015

(65) Prior Publication Data
US 2017/0112754 A1    Apr. 27, 2017

Related U.S. Application Data (60) Provisional application No. 62/007,768, filed on Jun. 4, 2014.

(51) Int. Cl.
| | |
|---|---|
| A61K 8/65 | (2006.01) |
| A61K 8/86 | (2006.01) |
| A61K 9/08 | (2006.01) |
| A61K 31/77 | (2006.01) |
| A61K 47/34 | (2017.01) |
| A61L 15/32 | (2006.01) |
| A61L 15/44 | (2006.01) |
| A61K 9/00 | (2006.01) |
| A61L 26/00 | (2006.01) |
| A61K 38/17 | (2006.01) |
| A61Q 7/00 | (2006.01) |
| A61Q 19/00 | (2006.01) |
| C08G 65/333 | (2006.01) |

(52) U.S. Cl.
CPC ............ *A61K 8/86* (2013.01); *A61K 8/65* (2013.01); *A61K 9/0014* (2013.01); *A61K 9/08* (2013.01); *A61K 31/77* (2013.01); *A61K 38/1748* (2013.01); *A61K 47/34* (2013.01); *A61L 15/32* (2013.01); *A61L 15/44* (2013.01); *A61L 26/0047* (2013.01); *A61L 26/0066* (2013.01); *A61Q 7/00* (2013.01); *A61Q 19/00* (2013.01); *A61Q 19/007* (2013.01); *C08G 65/33396* (2013.01); *A61L 2300/252* (2013.01); *A61L 2300/412* (2013.01)

(58) Field of Classification Search
None
See application file for complete search history.

(56) References Cited

U.S. PATENT DOCUMENTS

| | | | | |
|---|---|---|---|---|
| 5,679,329 | A * | 10/1997 | Dupuis | A61K 8/8152 424/70.14 |
| 6,410,017 | B1 | 6/2002 | Weisgerber et al. | |
| 9,730,881 | B2 * | 8/2017 | Meyer | A61K 8/65 |
| 2004/0062748 | A1 * | 4/2004 | Martinez | A61K 9/1271 424/85.1 |
| 2008/0038327 | A1 * | 2/2008 | Kelly | A61K 38/39 424/445 |
| 2008/0089930 | A1 | 4/2008 | Siller-Jackson et al. | |
| 2008/0159975 | A1 * | 7/2008 | Nho | A61K 8/042 424/70.11 |
| 2009/0165812 | A1 | 7/2009 | Resnick et al. | |
| 2010/0092416 | A1 * | 4/2010 | Luengo | A61Q 1/10 424/70.6 |
| 2010/0196302 | A1 * | 8/2010 | Vermelho | C12P 21/06 514/1.1 |
| 2011/0070276 | A1 * | 3/2011 | Cowsar | A61K 8/64 424/402 |
| 2012/0014887 | A1 | 1/2012 | Fournial et al. | |
| 2012/0156135 | A1 | 6/2012 | Farokhzad et al. | |

FOREIGN PATENT DOCUMENTS

| | | |
|---|---|---|
| CN | 102952246 | 3/2013 |
| WO | 2000/076437 | 12/2000 |
| WO | 2003064449 | 8/2003 |
| WO | 2008130607 | 10/2008 |
| WO | 2011141882 | 11/2011 |
| WO | 2014022163 | 2/2014 |
| WO | WO 2014/022163 | * 2/2014 |

OTHER PUBLICATIONS

CN102952246A (machine translation) (Year: 2011).*
Truebotanicals (downloaded on Nov. 4, 2019 from URL:< https://ritual.truebotanicals.com/skin-care/what-is-skin-barrier/>) (Year: 2019).*
Villa et al. (BMC Biotechnology 2013, 13:15) (Year: 2013).*
Cosmetic Ingredient review (Hydrolyzed Source Proteins as Used in Cosmetics, May 21, 2012) (Year: 2012).*
Ng et al. (PLoS Genet. 2012;8(7):e1002748) (Year: 2012).*
Of Jina et al. (ANZ J Surg. May 2015;85(5):378-80, abstract only) (Year: 2015).*
Lola's secret beauty blog (Downloaded from URL:< http://www.lolassecretbeautyblog.com/2013/10/>, Oct. 31, 2013) (Year: 2013).*
Barba et al. (Skin Res Technol. May 2008;14(2):243-8) (Year: 2008).*
Kaya et al. (Genes & Development, 11:996-1007, 1997) (Year: 1997).*
Moll et al. (Histochem Cell Biol (2008) 129:705-733) (Year: 2008).*
A T Batzer, Maximising Healing Outcomes with Keratin Based Wound Products, Proceedings of SAWC, Atlanta, GA, Apr. 2012.
Davidson, Andrew, et al. "Do functional keratin dressings accelerate epithelialization in human partial thickness wounds? A randomized controlled trial on skin graft donor sites." Eplasty 13, 2013.

(Continued)

*Primary Examiner* — Sergio Coffa
(74) *Attorney, Agent, or Firm* — Stetina, Brunda, Garred and Brucker (57) ABSTRACT

Provided herein are methods for improving skin quality in a subject comprising administering to the skin a pharmaceutical composition comprising a polypeptide covalently bound to a hydrophilic polymer and/or a polysaccharide covalently bound to a hydrophilic polymer.

17 Claims, 1 Drawing Sheet

(56) References Cited

OTHER PUBLICATIONS

S Davis, R Perez, Y Rivas, J Gil, J Valdes, and R Kirsner, The effect of a keratin based dressing on the epithelialization of deep partial thickness wounds, Journal of the American Academy of Dermatology Mar. 2009 (vol. 60, Issue 3, Supplement 1, p. AB201).
Hammond, C. E., M. Than, and J. W. Walker. "From the Laboratory to the Leg: Patients' and Nurses' Perceptions of Product Application Using Three Different Dressing Formats." Wound Practice & Research: Journal of the Australian Wound Management Association 18.4:189, 2010.
International Search Report and Written Opinion of the International Searching Authority, Application No. PCT/US2015/034199, dated Aug. 26, 2015, 7 pages.
International Preliminary Report on Patentability, Application No. PCT/US2015/034199, dated Dec. 15, 2016, 6 pages.
F Loan, C Marsh, S Cassidy, J Simcock, Keratin dressings for effective wound care management in acute superficial and partial thickness burn injuries. Proceedings of SAWC, Denver, CO, May 2013.
R Kirsner, S Cassidy, C Marsh, R Kelly, Use of a Keratin-Based Wound Dressing in the Management of Wounds in a Patient with Recessive Dystrophic Epidermolysis Bullosa, J. Advances in Skin and Wound Care, 25, 9, 400-403, 2012.
R.Kirsner Use of topical keratin gel by patients with epidermolysis bullosa, Journal of the American Academy of Dermatology, Mar. 2009 (vol. 60, Issue 3, Supplement 1, p. AB202).
Pechter, Patricia M., et al. "Keratin dressings speed epithelialization of deep partial-thickness wounds." Wound Repair and Regeneration 20.2:236-242, 2012.
Poranki, et al., Assessment of deep partial thickness burn treatment with keratin biomaterial hydrogels in a swine model, BioMed Research International vol. 2016, Article ID 1803912, 10 pages, Oct. 2016.
L Tang, J Ollague Sierra, R Kelly, R S Kirsner, J Li, Wool-derived keratin stimulates human keratinocyte migration and types IV and VII collagen expression, Experimental Dermatology, 21, 5, 2012, DOI: 10.1111/j.1600-0625.2012.01505.x.
M Than, R Smith, S Cassidy, R Kirsner, R Kelly, C Marsh, A Maderal, Use of Keragel in the Management of Recessive Dystrophic Epidermolysis Bullosa. Journal of Dermatological Treatment, epub Jan. 21, 2012.
A C Vivas, A D Maderal, M P Than, R S Kirsner Letter: Designing clinical trials to bring wound products to market. Int Wound J. 3 pages, 2011.
Extended European Search Report dated Dec. 12, 2017, from European Application No. 15802421.6, 8 pages.
English translation of Office Action dated Jan. 8, 2019, from corresponding JP Patent Application No. 2017-516264, 8 pages.
English translation of First Office Action and Search Report dated Dec. 3, 2019, from corresponding ON Patent Application No. 201580033514.X, 27 pages.
Verhoef, Johan J.F. et al., "Questioning the Use of PEGylation for Drug Delivery", Drug Deliv Transl Res. Dec. 2013; 3(6): 499-503.
Spectrum Safety Data Sheet, dated Apr. 13, 2016, 12 pages.

* cited by examiner

COMPOSITIONS AND METHODS FOR IMPROVING SKIN QUALITY

CROSS REFERENCE TO RELATED APPLICATIONS

This application is a national stage application filed under 35 U.S.C. § 371 of PCT/US2015/034199 filed Jun. 4, 2015, which claims the priority benefit of U.S. Provisional Patent Application Ser. No. 62/007,768 filed on Jun. 4, 2014.

BACKGROUND OF THE INVENTION

Field of the Invention

The invention relates to the field of skin treatment.

Description of Related Art

The integument or skin is the largest organ of the body, making up 16% of body weight, with a surface area of 1.8 m². The skin has several functions, the most important being to form a physical barrier to the environment, allowing and limiting the inward and outward passage of water, electrolytes and various substances while providing protection against micro-organisms, ultraviolet radiation, toxic agents and mechanical insults. There are three structural layers to the skin: the epidermis, the dermis and subcutis. The epidermis comprises five layers: stratum corneum, stratum lucidum, stratum granulosum, stratum spinosum, and stratum basale.

The stratum corneum is the outermost of the five layers of the epidermis and is largely responsible for the vital barrier function of the skin. The structure of the stratum corneum has been described as a "brick and mortar" type structure. In this analogy, the comeocytes are the bricks. A comeocyte is a protein complex that is made of tiny threads of keratin in an organized matrix. The keratin can hold large amounts of water between the fibers/threads. The stratum corneum contains about 12-16 layers of corneocytes and each comeocyte has a mean thickness of approximately 1 micrometer.

The "mortar" between the corneocytes contains free fatty acids and ceramides that are released from lamellar bodies in keratinocytes as they mature to the stratum corneum. Because there are two types of lipids, this layer is referred to as a lamellar lipid bilayer. This lipid bilayer plays a major role in maintaining the barrier properties of the skin. Corneocytes also contain a natural moisturizing factor (NMF), which is a collection of water-soluble compounds. These compounds compose approximately 20-30% of the dry weight of the corneocyte. NMF components absorb water from the atmosphere and combine it with their own water content allowing the outermost layers of the stratum corneum to stay hydrated despite exposure to the elements.

Accordingly, the epidermis, and the stratum corneum in particular, plays a large role in defending a body against infection and preventing excessive water loss through the skin. Because the risk of infection and water loss rises dramatically when the epidermal barrier is breached, natural processes for wound healing exist in order to repair the breach as quickly as possible and protect the body. It is becoming clear that smaller and less obvious breaches of the epidermis are also problematic. Studies of atopic dermatitis indicate that, at least in some cases, the condition is associated with a genetic defect in the epidermal barrier which allows irritants, microbes and allergens to penetrate the skin and cause the adverse reactions commonly associated with atopic dermatitis.

The inability of a body's natural processes to repair an epidermal breach can be costly. Non-healing wounds affect about 3 to 6 million people in the United States, with persons 65 years and older accounting for 85% of these events. Non-healing wounds result in enormous health care expenditures, with the total cost estimated at more than $3 billion per year. Further, atopic dermatitis now affects 10-20% of children in the United States and direct healthcare costs exceeded $3 billion per year in 2013 according to the National Institute of Arthritis and Musculoskeletal and Skin Disease.

There is a need, therefore, to develop compositions and methods for the protection of skin, and for improving skin quality such as dryness, redness, scaliness, itchiness, rash, ability to resist or manage infection, or ability to heal a wound.

SUMMARY OF THE INVENTION

Provided herein are compositions and methods that solve the problems or inadequacies of the prior art. In particular, provided herein are methods for improving skin quality in a subject comprising administering to the skin a pharmaceutical composition comprising a polypeptide covalently bound to a hydrophilic polymer and/or a polysaccharide covalently bound to a hydrophilic polymer. It is a surprising finding of the present invention that a composition containing a keratin polypeptide and a hydrophilic polymer improves one or more skin qualities when applied to the skin. Skin qualities include, but are not limited to, dryness, redness, scaliness, itchiness, rash, ability to resist or manage infection, and ability to heal a wound.

In some embodiments, the hydrophilic polymer has a formula selected from:

wherein $R_1$ is hydroxyl, carboxyl, ethylamine, 2-pyrrolidone, hydroxyethyl methacrylic acid, methylamine, phosphonic acid, sulfonic acid, hydroxyl, or $SO4^-$; wherein $R_2$ is hydrogen, methyloxazoline, ethyloxazoline, or propyloxazoline; and wherein "n" is between 1 and 1,500. In some embodiments, the "n" in formula Ia, Ib or Ic is between 1 and 1000, 1 and 500, 1 and 250, or 1 and 125. In some embodiments, the "n" in formula Ia, Ib or Ic is between about 100 and about 125. In still other embodiments, the "n" is about 114.

DETAILED DESCRIPTION OF THE INVENTION

Definitions

Terms used throughout this application are to be construed with ordinary and typical meaning to those of ordinary skill in the art. However, Applicants desire that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

The term "atopic dermatitis" is used herein to refer to a skin condition also known as eczema that can include or lead to one or more of, dryness, rash, redness, itchiness, and fluid-filled sores.

A "composition" is intended to include a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "covalently bound" means that a covalent bond exists between a portion of the hydrophilic polymer and the polypeptide, or vice-versa. Accordingly, the term "covalently bound" refers to both direct covalent bonds (a sharing of pairs of electrons between the atoms of the hydrophilic polymer and the polypeptide) and indirect covalent bonds (a sharing of pairs of electrons between atoms of the hydrophilic polymer and the composition comprising the polypeptide, or vice-versa).

The term "epidermal breach" refers to a loss or reduction of a barrier property in at least the stratum corneum of the skin. A "barrier property" refers to an ability to impede the entry or exit of a compound or microorganism through the skin. In some embodiments, the epidermal breach comprises a wound. In other embodiments, the epidermal breach is that caused by atopic dermatitis. The term "epidermal breach" further includes burns, sores including mouth sores such as canker sores, and surgical incisions including cosmetic surgery incisions and oral surgery incisions.

"Mammal" for purposes of treatment refers to any animal classified as a mammal, including human, domestic and farm animals, nonhuman primates, and zoo, sports, or pet animals, such as dogs, horses, cats, cows, etc.

A "pharmaceutical composition" is intended to include the combination of an active agent with a pharmaceutically acceptable carrier or excipient, inert or active, making the composition suitable for diagnostic or therapeutic use in vivo or ex vivo.

The term "pharmaceutically acceptable carrier" means a carrier or excipient that is useful in preparing a pharmaceutical composition that is generally safe and non-toxic, and includes a carrier that is acceptable for veterinary and/or human pharmaceutical use. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below. The pharmaceutical compositions also can include preservatives. A "pharmaceutically acceptable carrier" as used in the specification and claims includes both one and more than one such carrier.

The terms "therapeutically effective amount" or "therapeutically effective dose" refer to the amount of a compound such as a keratin-hydrophilic polymer composition that will elicit the biological or medical response of a tissue, system, animal, or human that is being sought by the researcher, veterinarian, medical doctor or other clinician over a generalized period of time. In some embodiments, a desired response is a skin quality improvement. In some instances, a desired biological or medical response is achieved following administration of multiple or dosages of the composition to the subject over a period of days, weeks, or years.

The term "subject" is defined herein to include animals. In some embodiments, the animal is a non-mammal such as a reptile or a bird. In some embodiments, the animal is a mammal, including, but not limited to, primates (e.g., humans), cows, sheep, goats, horses, dogs, cats, rabbits, rats, mice and the like. In some embodiments, the subject is a human. In some embodiments, the subject is a child.

The term "wound" refers herein to an injury to skin wherein at least a portion of the epidermal layer of the skin is damaged. The term "wound" includes a first-degree abrasion, a second-degree abrasion, a third-degree abrasion, a laceration, an incision, a puncture wound, and a penetration wound.

DETAILED DESCRIPTION

Provided herein are methods for improving skin quality in a subject comprising administering to the skin a pharmaceutical composition comprising a polypeptide covalently bound to a hydrophilic polymer and/or a polysaccharide covalently bound to a hydrophilic polymer. The polypeptides bound to the hydrophilic polymer include, but are not limited to, polypeptides of keratin, collagen, elastin, fibroin, milk-derived proteins such as casein, beta-lactoglobulin and alpha-lactalbumin, and grain proteins such as wheat protein. Hydrophobic polypeptides such as keratin may be preferred in certain embodiments. Also provided herein are compositions comprising a hydrophilic polymer covalently bound to a polysaccharide such as chitosan, chitin, or chitin glucan.

It is a surprising finding of the present invention that a composition containing a keratin polypeptide and a hydrophilic polymer improves one or more skin qualities when applied to the skin. Skin qualities include, but are not limited to, dryness, redness, scaliness, itchiness, rash, ability to resist or manage infection, and ability to heal an epidermal breach including a wound. The term "keratin" refers to a family of fibrous structural proteins that are found in the hair, skin, nails, claws and hooves of mammals (α-keratins) and in the scales, claws and shells of reptiles, the feathers, beaks, and claws of birds and the quills of porcupines (β-keratins). Alpha-keratins are also known as cytokeratins and are further subdivided into soft α-keratins (epithelial cytokeratins) and hard α-keratins (trichocyte keratins). All keratins are heteropolymers of type I and type II keratins. The HUGO Gene Nomenclature Committee identifies the following as known keratin polypeptide encoding genes: KRT1, KRT2, KRT3, KRT4, KRT5, KRT6A, KRT6B, KRT6C, KRT7, KRT8, KRT9, KRT10, KRT12, KRT13, KRT14, KRT15, KRT16, KRT17, KRT18, KRT19, KRT20, KRT23, KRT24, KRT25, KRT26, KRT27, KRT28, KRT31, KRT32, KRT33A, KRT33B, KRT34, KRT35, KRT36, KRT37, KRT38, KRT39, KRT40, KRT71, KRT72, KRT73, KRT74, KRT75, KRT76, KRT77, KRT78, KRT79, KRT80, KRT81, KRT82, KRT83, KRT84, KRT85, KRT86, KRT222. Accordingly, a keratin polypeptide of the present invention may be encoded by one or more genes selected from KRT1, KRT2, KRT3, KRT4, KRT5, KRT6A, KRT6B, KRT6C, KRT7, KRT8, KRT9, KRT10, KRT12, KRT13, KRT14, KRT15, KRT16, KRT17, KRT18, KRT19, KRT20, KRT23, KRT24, KRT25, KRT26, KRT27, KRT28, KRT31, KRT32, KRT33A, KRT33B, KRT34, KRT35, KRT36, KRT37, KRT38, KRT39, KRT40, KRT71, KRT72, KRT73, KRT74, KRT75, KRT76, KRT77, KRT78, KRT79, KRT80, KRT81, KRT82, KRT83, KRT84, KRT85, KRT86, and KRT222.

As used herein, the term "polypeptide" is used in its broadest sense to refer to a compound of two of more subunit amino acids, amino acid analogs, or peptidomimetics. The subunits may be linked by peptide bonds. In another embodiment, the subunits may be linked by other bonds, e.g., ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids may be referred to as an oligopeptide if the peptide chain is short, e.g., less than about 25 amino acids. The term "polypeptide" can include full-length naturally occurring proteins as well as functional fragments of those proteins. Protein fragments are functional when they achieve the desired result of the full-length protein in the context of the present invention. For example, a keratin fragment that is covalently bound to a hydrophilic polymer is encompassed by the present invention when the keratin-hydrophilic polymer provides a skin improvement effect when applied to skin using the methods of the present invention. A polypeptide can be derived from natural sources or synthetically prepared, including through the use of large-scale protein expression mechanisms. The polypeptides may be hydrolyzed or non-hydrolyzed, and in some embodiments, the polypeptides are non-hydrolyzed.

It should be understood that the keratin polypeptide can be naturally derived or synthetically prepared. The keratin polypeptide can be purified from various natural sources or commercially obtained. The keratin polypeptide can have a molecular weight from about 0.5 kDa to about 60 kDa, or from about 2 kDa to about 6 kDa, or from about 20 kDa to about 40 kDa. In some embodiments, the keratin polypeptide is about 5 kDa. In some embodiments, the keratin polypeptide is about 45 kDa to about 55 kDa. In still other embodiments, the keratin polypeptide is about 52 kDa.

As used herein, the term "hydrophilic polymer" includes polypeptides, carbohydrates, nucleic acids, poly(ethylene glycol), poly(oxazoline), poly(vinylpyrrolidone), poly(acrylamide), poly(acrylic acid), poly(allylamine), poly(hydroxyethyl methacrylate), poly(ethyleneimine), poly(vinylphosphonic acid), poly(vinyl sulfate), poly(vinylsulfonic acid), poly(vinyl alcohol), glycerol propoxylate, hydroxyethyl starch (HES). In one embodiment, the hydrophilic polymer is a synthetic hydrophilic polymer selected from the group consisting of: poly(ethylene glycol), poly(oxazoline), poly(vinylpyrrolidone), poly(acrylamide), poly(acrylic acid), poly(allylamine), poly(hydroxyethyl methacrylate), poly(ethyleneimine), poly(vinylphosphonic acid), poly(vinyl sulfate), poly(vinylsulfonic acid), poly(vinyl alcohol), glycerol propoxylate, and hydroxyethyl starch (HES). In some embodiments, the molecular weight of the hydrophilic polymer is between about 0.5 and about 80 kDa, between about 0.5 and about 40 kDa, or between about 0.5 and about 10 kDa. In some embodiments, the molecular weight of the hydrophilic polymer is between about 2 and about 10 kDa. In some embodiments, the molecular weight of the hydrophilic polymer is between about 20 and about 40 kDa. In one embodiment, the molecular weight of the hydrophilic polymer is about 5 kDa. In another embodiment, the molecular weight of the hydrophilic polymer is about 30 kDa.

In other or further embodiments, the hydrophilic polymer has a formula selected from:

Ia

, and

Ib

;

Ic wherein $R_1$ is hydroxyl, carboxyl, ethylamine, 2-pyrrolidone, hydroxyethyl methacrylic acid, methylamine, phosphonic acid, sulfonic acid, hydroxyl, or $SO_4^-$; wherein $R_2$ is hydrogen, methyloxazoline, ethyloxazoline, or propyloxazoline; and wherein "n" is between 1 and 1,500. In some embodiments, the "n" in formula Ia, Ib or Ic is between 1 and 1000, 1 and 500, 1 and 250, or 1 and 125. In some embodiments, the "n" in formula Ia, Ib or Ic is between about 100 and about 125. In still other embodiments, the "n" is about 114. In still further embodiments, the "n" in formula Ia, Ib or Ic may be selected from 1, 2, 3, 4, 5, 6, 7, 8, 9, 10, 11, 12, 13, 14, 15, 16, 17, 18, 19, 20, 21, 22, 23 and 24.

In yet another embodiment, the hydrophilic polymer is covalently bound to a keratin polypeptide and the hydrophilic polymer has a formula of:

Ia wherein n is between 1 and 1,500. In some embodiments, the "n" in formula Ia, Ib or Ic is between 1 and 1000, 1 and 500, 1 and 250, or 1 and 125. In some embodiments, the "n" in formula Ia, Ib or Ic is between 100 and 125. In still other embodiments, the "n" is about 114. In still further embodiments, the "n" in formula Ia, Ib or Ic may be selected from 1, 2, 3, 4, 5, 6, 7, 8, 9, 10, 11, 12, 13, 14, 15, 16, 17, 18, 19, 20, 21, 22, 23 and 24.

The compounds of formula Ia are known to those of skill in the art as polyethylene glycol, or PEG, compounds. There are a wide range of PEG compounds that can be used—these compounds can be linear or branched, reactive on one or both ends (mono- or bi-functional), or non-reactive in the traditional sense. The PEG compounds encompassed by the present invention are capable of being covalently bound to a polypeptide at reactive moiety on the polypeptide, or a polypeptide modified to include such a reactive moiety, however, the invention is not limited by the covalent attachment method. In some embodiments, the PEG compound is functionalized to allow reaction with the polypeptide. In some embodiments, the hydrophilic polymer is a PEG compound that covalently binds a polypeptide at a primary amine (e.g. a lysine residue). In other embodiments, the hydrophilic polymer is a PEG compound that covalently binds a polypeptide at a sulfhydryl (e.g. a cysteine residue).

Non-limiting examples of hydrophilic PEG polymers that fall within the present invention are MS(PEG)$_4$ (Thermo Scientific, Rockford, Ill., USA), MS(PEG)$_8$ (Thermo Scientific, Rockford, Ill., USA), MS(PEG)$_{12}$ (Thermo Scientific, Rockford, Ill., USA), MS(PEG)$_{24}$ (Thermo Scientific, Rockford, Ill., USA), TMS(PEG)$_{12}$ (Thermo Scientific, Rockford, Ill., USA), TMM(PEG)$_{12}$ (Thermo Scientific, Rockford, Ill., USA), MM(PEG)$_{12}$ (Thermo Scientific, Rockford, Ill., USA), MM(PEG)$_{24}$ (Thermo Scientific, Rockford, Ill., USA), and other N-hydroxysuccinimide functionalized PEGs, mPEG-Succinimidyl-Succinate (molecular weight of 2, 5, 10 20 or 30 kDa) (Laysan Bio., Inc., Arab, Ala., USA), mPEG-Nitrophenyl carbonate (molecular weight of 2, 5, 10, 20, or 30 kDa) (Laysan Bio., Inc., Arab, Ala., USA), mPEG-Succinimidyl Valerate (molecular weight of 2, 5, 10, 20, 30, 40, or 60 kDa) (Laysan Bio., Inc., Arab, Ala., USA), and mPEG-Succinimidyl Glutarate (molecular weight of 2, 5, 10, 20 or 30 kDa) (Laysan Bio., Inc., Arab, Ala., USA). "Branched" polyethylene glycol compositions include TMS (PEG)$_{12}$, TMM(PEG)$_{12}$, and any other multi-armed polyethylene glycol compositions. In one embodiment, the hydrophilic polymer is an mPEG-Succinimidyl-Succinate polymer that is about 5 kDa and wherein "n" is about 114.

Figure 1:
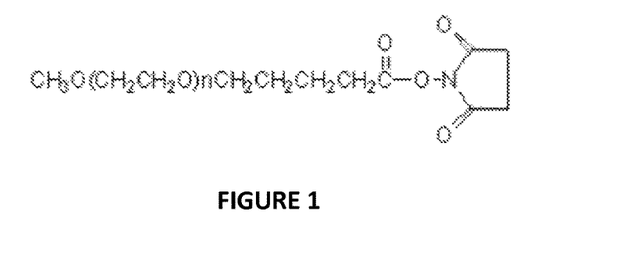
FIG. 1 is a chemical structure of a functionally reactive succinimidyl valerate in the terminal position of a polyethylene glycol polymer.

Functionally reactive moieties present or introduced into polypeptides or polysaccharides of the present invention can react with functionally reactive moieties present or introduced into the hydrophilic polymers of the present invention to form covalent bonds between the polypeptide and hydrophilic polymer. For example, functionally reactive moieties useful in the present invention include those used in click chemistry, maleimide chemistry, and NHS-esters, among others. Functionally reactive moieties involved in click chemistry include, but are not limited to, azides and alkynes that form a triazole ring via the Huisgen cycloaddition process (see U.S. Pat. No. 7,375,234, incorporated herein in its entirety). The maleimide chemistry involves reaction of the maleimide olefin with a nucleophile, such as —OH, —SH or —NH$_2$, to form a stable bond. Other functionally reactive moieties include those described in *Bioconjugate Techniques*, Greg T. Hermanson, Academic Press, 2nd ed., 2008 (incorporated in its entirety herein). In the case of the hydrophilic polymer polyethylene glycol, by way of non-limiting example, functionally active moieties are typically introduced at one or both ends of the polyethylene glycol polymer, as shown in FIG. 1 where the functionally reactive succinimidyl valerate is shown in the terminal position of a polyethylene glycol polymer.

Some non-limiting examples of the reaction of functionally reactive moieties present or introduced into hydrophilic polymers and some functionally reactive moieties typically found or introduced into polypeptides or polysaccharides are set forth in Table 1.

TABLE 1

| Illustrative Functionally Reactive Moieties on Polypeptide/ Polysaccharide Y | Exemplary Functionally Reactive Moieties on Hydrophilic Polymer X | Covalent Product Y—X |
| --- | --- | --- |
| Y—COOH | HO—X (hydroxyl or activated forms thereof (e.g., tresylate, mesylate etc.)) | Y—C(=O)O—X |
| Y—COOH | HS—X (thiol) | Y—C(=O)S—X |
| Y—SH | | Y—S—S—X |
| Y—SH | R'—S—S—X (disulfide) | Y—S—S—X |
| Y—SH | (pyridyl)-S—S—X (dithiopyridyl) | Y—S—S—X |
| Y—NH$_2$ | H(O=)C—X aldehyde | Y—N=CH—X or Y—NH—CH$_2$—X following reduction |
| Y—NH$_2$ | (HO)$_2$HC—X aldehyde hydrate | Y—N=CH—X or Y—NH—CH$_2$—X following reduction |

TABLE 1-continued

| Illustrative Functionally Reactive Moieties on Polypeptide/ Polysaccharide Y | Exemplary Functionally Reactive Moieties on Hydrophilic Polymer X | Covalent Product Y—X |
|---|---|---|
| Y—NH$_2$ | (R'O)$_2$CH—X  or  acetal | Y—N=CH—X or Y—NH—CH—X following reduction |
| Y—NH$_2$ | R'OCH(OH)—X or hemiacetal | Y—N=CH—X or Y—NH—CH—X following reduction |
| Y—NH$_2$ | R'(O=)C—X ketone | Y—N=CR'—X or Y—NH—C(R')H—X following reduction |
| Y—NH$_2$ | (R'O)$_2$C(R')—X  or  ketal | Y—N=C(R')—X or Y—NH—C(R')H—X following reduction |
| Y—NH$_2$ | R'OC(R')OH—X hemiketal | Y—N=C(R')—X or Y—NH—C(R')H—X following reduction |
| Y—NH$_2$ | R'(S=)C—X ketone thione (thioketone) | Y—N=C(R')—X or Y—NH—C(R')H—X following reduction |
| Y—NH$_2$ | (R'O)(R'S)C(R')—X  or  monothioketal | Y—N=C(R')—X or Y—NH—C(R')H—X following reduction |
| Y—NH$_2$ | R'SC(R')(SH)—X or dithiohemiketal | Y—N=C(R')—X or Y—NH—C(R')H—X following reduction |
| Y—NH$_2$ | (R'S)$_2$C(R')—X  or  dithioketal | Y—N=C(R')—X or Y—NH—C(R')H—X following reduction |
| Y—SH |  epoxide (oxirane) | Y—S—CH$_2$—C(OH)(R")—X— |
| Y—OH Y—COOH (anion) Y—NHR" | | Y—O—CH$_2$—C(OH)(R")—X— Y—C(=O)O—CH$_2$—C(OH)(R")—X— Y—NR"—CH$_2$—C(OH)(R")—X— |
| Y—SH |  thioepoxide | Y—S—CH$_2$—C(SH)(R")—X |
| Y—OH Y—COOH (anion) Y—NHR" | | Y—O—CH$_2$—C(SH)(R")—X— Y—C(=O)O—CH$_2$—C(SH)(R")—X— Y—NR"—CH$_2$—C(SH)(R")—X— |

TABLE 1-continued

| Illustrative Functionally Reactive Moieties on Polypeptide/ Polysaccharide Y | Exemplary Functionally Reactive Moieties on Hydrophilic Polymer X | Covalent Product Y—X |
|---|---|---|
| Y—SH | HO—(C=O)—X<br>carboxyl | Y—S—(C=O)—X |
| Y—OH<br>Y—NHR"<br>Y—SH | (alcohol)-(C=O)—X<br>carboxylic acid ester<br>(alcohol indicates an esterified suitable alcohol leaving group e.g., p-nitrophenyl) | Y—O—(C=O)—X<br>Y—N(R")—(C=O)—X<br>Y—S—(C=O)—X |
| Y—OH<br>Y—NHR" | | Y—O—(C=O)—X<br>Y—NR"—(C=O)—X |
| Y—NH$_2$ | <br>N-hydroxysuccinimide ester | Y—NH—R'''—X |
| Y—SH | <br>R = H, CH$_3$ | <br>R = H, CH$_3$ |
| Y—NH$_2$ | <br>1-benzotriazole ester | Y—NH—R'''—X |
| Y—NH$_2$<br>Y—(C=NH)—O—((CH$_2$)$_{1-3}$)—CH$_3$<br>(imidoester) | CH$_3$—((CH$_2$)$_{1-3}$)—O(C=NH)—X<br>(imidoester)<br>H$_2$N—X | Y—NH—(C=NH)—X<br>(amidine)<br>Y—(C=NH)—HN—X<br>(amidine) |
| Y—COOH | H$_2$N—X<br>amine | Y—(C=O)—NH—X |
| Y—(C=O)—R" | | Y—(R")C=N—X or<br>Y—(R")CH—NH—X following reduction |
| Y—COOH | H$_2$N—(C=O)—NH—X<br>urea | Y—(C=O)—NH—(C=O)—NH—X |
| Y—(C=O)—R" | | Y—(R")C=N—(C=O)—NH—X or<br>Y—(R")CH—NH—(C=O)—NH—X<br>following reduction |
| Y—COOH | H$_2$N—(C=O)—O—X<br>carbamate | Y—(C=O)—NH—(C=O)—O—X |
| Y—(C=O)—R" | | Y—(R")CN—(C=O)—O—X or<br>Y—(R")CH—NH—(C=O)—O—X following reduction |
| Y—COOH | H$_2$N—(C=S)—NH—X<br>thiourea | Y—(C=O)—NH—(C=S)—NH—X |
| Y—(C=O)—R" | | Y—(R")C=N—(C=S)—NH—X or<br>Y—(R")CH—NH—(C=S)—NH—X<br>following reduction |
| Y—COOH | H$_2$N—(C=S)—O—X<br>thiocarbamate | Y—(C=O)—NH—(C=S)—O—X |
| Y—(C=O)—R" | | Y—(R")C=N—(C=S)—O—X or<br>Y—(R")CH—NH—(C=S)—O—X<br>following reduction |
| Y—(C=O)—R" | H$_2$N—HN—X | Y—(R")C=N—HN—X<br>hydrazone |

TABLE 1-continued

| Illustrative Functionally Reactive Moieties on Polypeptide/ Polysaccharide Y | Exemplary Functionally Reactive Moieties on Hydrophilic Polymer X | Covalent Product Y—X |
|---|---|---|
| Y—NH—NH$_2$ | R''—(O=C)—X | Y—NH—N=C(R'')—X<br>hydrazone |
| Y—NH$_2$ | O=C=N—X<br>isocyanate | Y—NH—(C=O)—NH—X |
| Y—OH | | Y—O—(C=O)—NH—X |
| Y—NH$_2$ | S=C=N—X<br>isothiocyanate | Y—NH—(C=S)—NH—X |
| Y—OH | | Y—O—(C=S)—NH—X |
| Y—SH | H$_2$C=CH—(C=O)—X<br>or<br>H$_2$C=C(CH$_3$)—(C=O)—X<br>alpha-beta unsubstituted carbonyls | Y—S—CH$_2$CH$_2$—(C=O)—X<br>Y—S—CH$_2$—CH(CH$_3$)—(C=O)—X |
| Y—SH | H$_2$C=CH—(C=O)O—X<br>alpha-beta unsubstituted carboxyl | Y—S—CH$_2$CH$_2$—(C=O)O—X |
| Y—SH | H$_2$C=C(CH$_3$)—(C=O)—O—X<br>alpha-beta unsubstituted carboxyls<br>(methacrylates) | Y—S—CH$_2$CH(CH$_3$)—(C=O)O—X |
| Y—SH | H$_2$C=CH—(C=O)NH—X<br>alpha-beta unsubstituted amides<br>(acrylamides) | Y—S—CH$_2$CH$_2$—(C=O)NH—X |
| Y—SH | vinylpyridine-X<br>(2- or 4-vinylpyridine) | Y—S—CH$_2$—CH$_2$-(pyridyl)-X |
| Y—SH | H$_2$C=CH—SO$_2$—X<br>(vinyl sulfone) | Y—S—H$_2$C—CH$_2$—SO$_2$—X |
| Y—SH | ClH$_2$C—CH$_2$—SO$_2$—L<br>(chloroethyl sulfone) | Y—S—H$_2$C—CH$_2$—SO$_2$—X |
| Y—SH | (halogen)-CH$_2$—(C=O)—O—X<br>(halogen)-CH$_2$—(C=O)—NH—X<br>(halogen)-CH$_2$—(C=O)—X<br>(halogen is preferably I or Br) | Y—S—CH$_2$—(C=O)—O—X<br>Y—S—CH$_2$—(C=O)—NH—X<br>Y—S—CH$_2$—(C=O)—X |
| Y—O(C=O)—CH$_2$-(halogen)<br>Y—NH(C=O)—CH$_2$-<br>(halogen)<br>Y—(C=O)—CH$_2$-(halogen)<br>(halogen is preferably<br>I or Br) | HS—X | Y—O(C=O)—CH$_2$—S—X<br>Y—NH(C=O)—CH$_2$—S—X<br>Y—(C=O)—CH$_2$—S—X |
| Y—SH | (halogen)-CH$_2$(C=O)O—X<br>(halogen)-CH$_2$(C=O)NH—X<br>(halogen)-CH$_2$(C=O)—X<br>(halogen is preferably I or Br) | Y—S—CH$_2$(C=O)O—X<br>Y—S—CH$_2$(C=O)NH—X<br>Y—S—CH$_2$(C=O)—X |
| Y—N$_3$ | H≡C—X |  |
| Y—N$_3$ |  |  |
| Y—N$_3$ |  |  |

TABLE 1-continued

| Illustrative Functionally Reactive Moieties on Polypeptide/ Polysaccharide Y | Exemplary Functionally Reactive Moieties on Hydrophilic Polymer X | Covalent Product Y—X |
|---|---|---|
| Y—SH |  |  |
| Y—NH$_2$ | (F$_5$—Ph)—OC(O)—X | Y—NH—C(O)—X |

R' is $C_{1-6}$ alkyl, $C_{3-6}$ cycloalkyl, or an aryl group having 5-8 endocyclic atoms;

R" is H, $C_{1-6}$ alkyl, $C_{3-6}$ cycloalkyl, or an aryl group having 5-8 endocyclic atoms;

R is a carbonyl derivative *—(C═O)—, *—(C═O)—(CH$_2$)$_{1-8}$—*—(C═O)—(CH$_2$)$_{1-8}$—S—S—, *—(C═O)—(CH$_2$)$_{1-8}$—(C═O)—O—, *—(C═O)—(CH$_2$)$_{1-8}$—O—(C═O)—, *—(C═O)—(CH$_2$)$_{1-8}$—(C═O)—NH—, or *—(C═O)—(CH$_2$)$_{1-8}$—NH—(C═O)—, or alternatively, R'" is a carbonyl derivative of the form *—(C═O)—O—(CH$_2$)$_{1-8}$—S—S—, *—(C═O)—O—(CH$_2$)$_{1-8}$—(C═O)—O—, *—(C═O)—O—(CH$_2$)$_{1-8}$—(C═O)—O—(CH$_2$)$_{1-8}$—*—(C═O)—O—(CH$_2$)$_{1-8}$—O—(C═O)—, *—(C═O)—O—(CH$_2$)$_{1-8}$—(C═O)—NH—, or *—(C═O)—O—(CH$_2$)$_{1-8}$—NH—(C═O)—, where "*" indicates the point of attachment to succinimidyl or benzotriazolyl groups;

X and Y are each the polypeptide and the hydrophilic polymer, respectively.

The keratin-hydrophilic polymer compounds described herein can be provided in a pharmaceutical composition. The pharmaceutical compositions include a therapeutically effective amount of a keratin-hydrophilic polymer compound described herein in combination with a pharmaceutically acceptable carrier. In some embodiments, the pharmaceutical composition has antimicrobial properties.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, University of the Sciences in Philadelphia, Lippincott, Williams & Wilkins, Philadelphia Pa., 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN (ICI, Inc.; Bridgewater, N.J.), polyethylene glycol (PEG), and PLURONICS (BASF; Florham Park, N.J.). To provide for the administration of such dosages for the desired therapeutic treatment, compositions disclosed herein can advantageously comprise between about 0.1% and 99% by weight of the total of one or more of a keratin-hydrophilic polymer composition based on the weight of the total composition including carrier or diluent.

The polypeptide-hydrophilic polymer and polysaccharide-hydrophilic polymer pharmaceutical compositions described above and elsewhere herein are administered to the skin of a subject for improving a quality of the skin. In some embodiments, the term "skin" includes nails. The term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intrasynovial, intrasternal, intrathecal, intrahepatic, intralesional, and intracranial injections or infusion techniques.

Dosage forms for topical administration of the pharmaceutical compositions described herein include ointments, gels, pastes, liquids, solutions, creams, oils, foams, mousses, powders, aerosols, and sprays. The pharmaceutical compositions may also be applied to wound dressings such as patches, band aids, and gauze materials. Thickening agents, emollients, and stabilizers can be used to prepare the topical pharmaceutical compositions of the present invention. Examples of thickening agents include petrolatum, beeswax, xanthan gum, or polyethylene glycol, humectants such as sorbitol, emollients such as mineral oil, lanolin and its derivatives, or squalene. The pharmaceutical compositions described herein are admixed under sterile conditions with a pharmaceutically acceptable carrier and any preservatives, buffers, thickening agents, cosmetic agents, sunscreen agents, or propellants as can be required.

The polypeptide-hydrophilic polymer and polysaccharide-hydrophilic polymer pharmaceutical compositions can be administered to the skin in a therapeutically effective amount. Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. In some embodiments, the keratin-hydrophilic polymer pharmaceutical compositions are applied to the skin once, twice, three times, four times, five times, six times or more in a day. The keratin-hydrophilic polymer pharmaceutical compositions can be administered to the skin for any period of time including, but not limited to, about one day, about two days, about three days, about four days, about five days, about six days, about 1 week, about 2 weeks, about 3 weeks, about four weeks or more.

Administration of a polypeptide-hydrophilic polymer and/or polysaccharide-hydrophilic polymer pharmaceutical composition to the skin in a therapeutically effective amount can result in an improvement of skin quality. Skin qualities include, but are not limited to, dryness, redness, scaliness, itchiness, rash, ability to resist or manage infection, and ability to heal an epidermal breach including an ability to heal a wound. In some embodiments, administration of a therapeutically effective amount of a polypeptide-hydrophilic polymer and/or polysaccharide-hydrophilic polymer pharmaceutical composition to an area of skin that exhibits dryness results in a reduction of the size or severity of the dryness. In some embodiments, administration of a therapeutically effective amount of a polypeptide-hydrophilic polymer and/or polysaccharide-hydrophilic polymer pharmaceutical composition to an area of skin that exhibits redness results in a reduction in the size or severity of the redness. In some embodiments, administration of a therapeutically effective amount of a polypeptide-hydrophilic polymer and/or polysaccharide-hydrophilic polymer pharmaceutical composition to an area of skin that exhibits a rash results in a reduction in the size or severity of the rash. In some embodiments, administration of a therapeutically effective amount of a polypeptide-hydrophilic polymer and/or polysaccharide-hydrophilic polymer pharmaceutical composition to an area of skin that exhibits itchiness results in a reduction in the size or severity of the itchiness. In some embodiments, administration of a therapeutically effective amount of a polypeptide-hydrophilic polymer and/or polysaccharide-hydrophilic polymer pharmaceutical composition to an area of skin that exhibits signs of an infection results in a reduction in the size or severity of the infection. In some embodiments, administration of a therapeutically effective amount of a polypeptide-hydrophilic polymer and/or polysaccharide-hydrophilic polymer pharmaceutical composition to an area of skin results in a reduction of the likelihood of the onset of an infection on the skin as compared to a control. In some embodiments, administration of a therapeutically effective amount of a polypeptide-hydrophilic polymer and/or polysaccharide-hydrophilic polymer pharmaceutical composition to an area of skin that contains a wound results in a faster or more complete reduction of the size of the wound as compared to a control. In some embodiments, administration of a therapeutically effective amount of a polypeptide-hydrophilic polymer and/or polysaccharide-hydrophilic polymer pharmaceutical composition to an area of skin that contains a wound results in decreased scarring at the site the wound.

In some embodiments, a therapeutically effective amount of polypeptide-hydrophilic polymer and/or polysaccharide-hydrophilic polymer pharmaceutical composition repairs or covers an epidermal breach in an area of skin to which it is administered. The repair or cover can be in whole or in part, but the effect is to increase a barrier property of the skin to which it is administered. In some embodiments, the barrier property relates to the inclusion or retention of water. In other or further embodiments, the barrier property relates to the exclusion of an allergen or irritant. Allergens include those that are a causative factor in atopic dermatitis. In still other or further embodiments, the barrier property relates to the exclusion of a microorganism. The term "microorganism" includes, but is not limited to, a bacterium, virus, and a fungus. Bacteria include, but are not limited to, those that commonly gain entry through a breach in the skin such as *Staphylococcus* species (e.g. *Staphylococcus aureus*) *Campylobacter* species, *Klebsiella pneumoniae*, *Escherichia coli*, *Capnocytophaga canimorsus*, *Vibrio vulnificus*, *Pseudomonas aeruginosa*, *Aeromonas hydrophila*, and *Salmonella* species.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All publications, patents and patent applications cited herein are hereby incorporated by reference in their entirety for all purposes.

EXAMPLES

Example 1

Preparation of Keratin-Polyethylene Glycol Composition

Keratin-polyethylene glycol compositions were prepared using the following equipment and materials:
Vortexer
Shaker
Pipettes (1000 micro liter)
Syringes (1 cc)
1.50 mL tubes
Weighing balance Mettler Malani Ser#172447
Fume hood
DPBS—Dulbecco's phosphate buffered saline (1×) Cat#14190-144, lot #901681,
Gibco Invitrogen.
N,N-dimethyl formamide, Cat # D119-500, lot #963760
MS(PEG)$_4$; [MS4] Cat#22341, lot # MI162217, Thermo Scientific (Pierce)
MS (PEG)$_{12}$; [MS12] Cat#22685, lot#MI162218, Thermo Scientific (Pierce)
MS (PEG)$_{24}$; [MS24] Cat#22687, lot#MH161869, Thermo Scientific (Pierce)
TMS (PEG)$_{12}$; [TMS12] Cat#22421, lot#MD157106, Thermo Scientific (Pierce)
Keratin [K] Cat# K3030, lot#1AG0185, Spectrum Using the above described materials and equipment, 10 mg of Keratin powder was placed in 1.5 mL centrifuge tubes (5 in number). The five samples were labeled K, K+MS4, K+MS12, K+MS24, and K+TMS12. One milliliter of phosphate buffered saline (PBS) was added to each of the 10 mg keratin samples and let shake for 45 minutes. Then 15 µL of about 250 mM MS4, MS12, MS24 and TMS12 pegylation stock solutions were added to each keratin sample tube and placed on a shaker for 30 minutes. The pegylation stock solutions were prepared using the following calculations:
Keratin M.W.=52.5 kDa
1 mL Conjugated protein X 10 mg/1 mL×1/52500×20/1=0.003809 mmol pegylated reagent. Then 0.003809× 1,000,000 µL/L×L/250 mmol=15.23.
About 15 µL of 250 mM pegylation reagent stock. Materials were equilibrated at room temperature.
MS4 1.1 mL DMF to 100 mg of stock MS4
MS12 485 µL DMF to 100 mg of stock MS12
MS24 230 µL DMF to 100 mg of stock MS24
TMS12 65 µL DMF to 100 mg of stock TMS12
The resultant solutions were stored in a freezer box with desiccant and returned to −20° C. freezer until used.

Example 2

Preparation of Keratin-Polyethylene Glycol (SVA) Compositions

Keratin-polyethylene glycol compositions were prepared using the following materials and equipment:
1. Pipettes
2. Syringes
3. 1.5 mL centrifuge tubes
4. Weighing balance Mettler
5. Methoxy-Poly (Ethylene Glycol)-Succinimidyl Valerate lot#120-176; Laysan Bio Inc. 5000 MW (SVA PEG) (5 k SVA PEG)
6. DPBS-Dulbecco's phosphate buffered saline cat#14190, lot#1048427, Gibco
7. Keratin Cat#K3030, lot#1AG0185, Spectrum Using the above-described materials and equipment, reaction sample was prepared having ratios of keratin polypeptide and SVA PEG polymer (1:1). The sample was prepared as follows:

In 1.5 mL centrifuge tubes 1 mL of DPBS was added. Sample tubes were labeled as follows:
1. K:P; 1:1=weighted out 50 mg of SVA PEG and added to 1 ml D-PBS+5 mg keratin Amount [5 mg] of keratin was then added to 1 mL D-PBS and shaken by hand to solubilize. Amount of SVA PEG was weighted out and added to the PBS-keratin solutions. The SVA PEG amount was 50 mg. Tube was then shaken by hand and sealed with parafilm.

Example 3

Administration of a Keratin-Polyethylene Glycol Composition to the Skin

The keratin-polyethylene glycol composition described in Example 1 was administered to the skin of various individuals aged 10 to 67, both male and female, over a period of days, weeks or months. Such administration resulted in decreased skin dryness, increased skin softness, and other skin improvements.

Example 4

Proliferation and Migration-Cell Culture Assay

Figure 2:
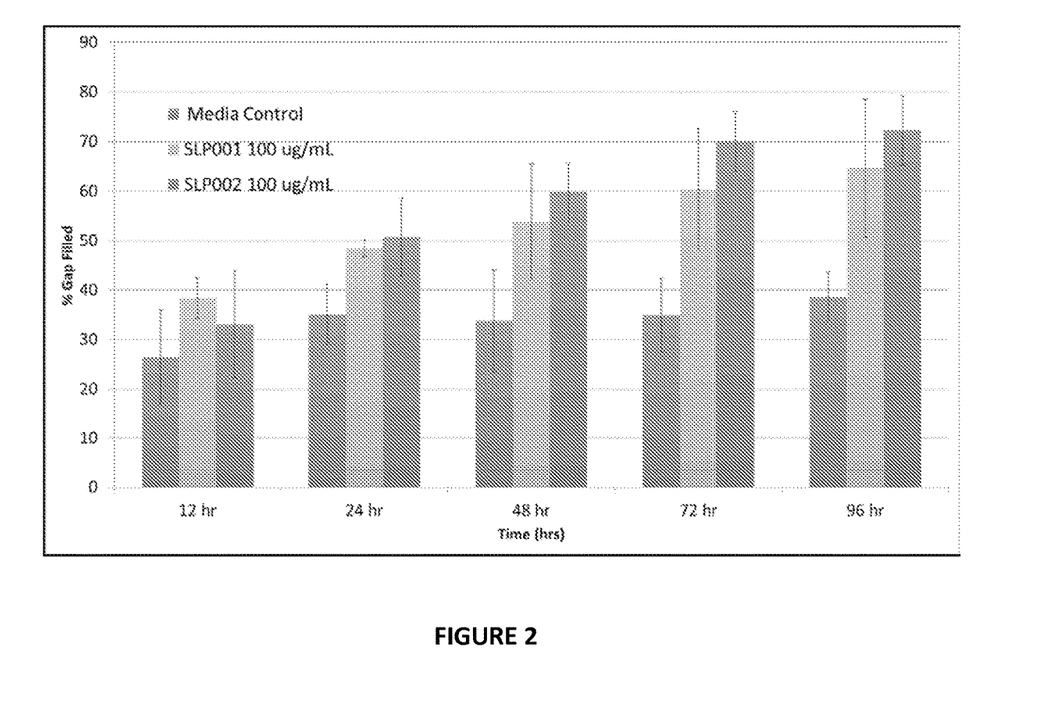
FIG. 2 is a graph showing the effect of 100 µg/mL of keratin-polyethylene glycol DPBS composition on primary human adult keratinocytes relative to media alone.

FIG. 2 is a graph showing the effect of 100 µg/mL of keratin-polyethylene glycol composition as described in Example 1 and Example 2 on primary human adult keratinocytes relative to media alone. The keratin-polyethylene glycol composition increased human keratinocyte migration in an Oris Cell Migration Assay. Primary keratinocytes were cultured in appropriate growth media with human keratinocyte growth supplement (HKGS) and pen/strep until cells reached confluence prior to seeding the assay.

The Oris Cell Migration Assay, a 96-well plate provided by Platypus Technologies, was seeded with 25,000 primary human keratinocytes with the Oris Cell Seeding Stoppers in place to prevent cell adhesion in the center of each well. The cells were incubated with growth medium plus HKSG for 24 hours then changed to media HKSG for 16 hours. When cells reached confluence the Oris Cell Seeding Stoppers were removed, exposing a uniform, circular "wound" in each well. Immediately upon removal of each stopper, test compounds were added at the indicated concentrations. SLP001 and SLP002 at 100, 50, 25, 10 µg/mL.

Cell migration (progressive wound gap closure) was recorded at time 0 hours (immediately after removing the stoppers), 24 hours, 48 hours, 72 hours, and 96 hours after treatment using brightfield microscopy. Migration was measured by the time and percentage of the wound gap covered by the cells that migrated in and filled up the wound gap, and quantified using CellProfiler Cell Image Analysis Software with the Cell Biolabs optimized add-ons.

Enhanced migration was observed within 24 hours and continued through 96 hours when keratinocytes were grown with keratin-polyethylene glycol composition treatment compared with control cells grown in media alone.

Example 5

A female of the age 12 with history of ingrown toenail infections, treated the infection developing nail with the keratin-polyethylene glycol composition as described in Example 2. The toe(s) were first cleansed and then dried. The keratin-polyethylene glycol composition was then applied and left uncovered for 24-48 hours. Within 8 hours there was noticeable improvement and pain of the wound was gone. After 48 hours there was no noticeable sign of the wound under or around the toe(s). Over a period of 1 year the application of the keratin-polyethylene glycol composition was applied during each incident and the incidents were lessened overtime to now the female only has ingrown toenail infections very rarely.

Example 6

Person in her 70s with thinning fine, mature hair had scalp lesions she received due to an anxious picking. She applied the keratin-polyethylene glycol described in Example 2 in a formulated topical solution, which are common excipients for application. The solution was applied to the scalp after each washing for a period of 2 months. This woman experienced new hair growth where the lesions had once previously been on her scalp and nearly all lesions had completely healed.

Example 7

A 73 year old reported she struck her hand knuckle on a table corner and the trauma split open a bleeding gash in her skin. With the application of the keratin-polyethylene glycol composition as described in Example 2, the laceration healed/stabilized in 24 hours with no recurrence of bleeding with movement of the joint/skin. One month later, skin was healed without scaring. The same week she had a second gash on a finger that was not treated. Scaring can still be seen at the second site. Thus, the inventive composition prevented scaring.

Example 8

A wound on a dog's foreleg was initially treated by a vet with oral antibiotics and topical ointment for 2 weeks with no improvement. Unfortunately, the dog also suffered with diarrhea and excess licking at the wound from both antibiotic treatments. After a one week "wash out period", the wound was cleansed each day prior to an application of keratin-polyethylene glycol composition as described in Example 2 once a day for 3 days. The wound was not covered. The dog was not bothered by the treatment. By the end of one month, the wound was gone and hair had grown back.

Example 9

A dog, bothered with constant dry skin, similar to the symptoms of atopic dermatitis, and incessantly scratching at herself, was bathed with cleaning solution followed with the keratin polyethylene glycol composition as described in Example 1 in topical formulated solution. The dog owner noticed a remarkable decrease in the dog's scratching plus the fur condition became soft, silky and fluffy. The dog had been bathed and conditioned every 2 or 3 weeks with sample keratin-polyethylene glycol composition as described in Example 1 in topical formulation for a duration of 3 months. No adverse effects were observed and the scratching subsided.

The invention claimed is:

1. A pharmaceutical composition comprising:
a therapeutically effective amount of a conjugate comprising a linear hydrophilic polymer covalently bound to a hydrolyzed keratin polypeptide;
wherein the linear hydrophilic polymer is covalently bound to the hydrolyzed keratin polypeptide via the linear hydrophilic polymer having a first end and a second end and the hydrolyzed keratin polypeptide having a functionally reactive moiety, the first end and second end being configured such that when the linear hydrophilic polymer is not covalently bound to the hydrolyzed keratin polypeptide, only the first end is operative to functionally react with the functionally relative moiety to form a covalent bond, and the second end is not operative to functionally react with the functionally relative moiety to form a covalent bond;
wherein the hydrolyzed keratin polypeptide comprises a natural or synthetic functional fragment from a full-length keratin protein;
wherein the functional fragment has a molecular weight from about 45 kDa to about 55 kDa;
wherein the conjugate is not water soluble;
wherein the full length keratin protein is encoded by a gene selected from KRT1, KRT2, KRT3, KRT4, KRT5, KRT6A, KRT6B, KRT6C, KRT7, KRT8, KRT9, KRT10, KRT12, KRT13, KRT14, KRT15, KRT16, KRT17, KRT18, KRT19, KRT20, KRT23, KRT24, KRT25, KRT26, KRT27, KRT28, KRT71, KRT72, KRT73, KRT74, KRT75, KRT76, KRT77, KRT78, KRT79, KRT80, KRT81, KRT82, KRT83, KRT84, or KRT85;
wherein the conjugate is formulated for administration to an epidermal breach; and
wherein the therapeutically effective amount of the conjugate is operative to enhance keratinocyte growth and migration at an epidermal breach.

2. The pharmaceutical composition of claim 1 wherein the conjugate has the formula Y—NH—R'''—X where Y—NH— is a remainder of the hydrolyzed keratin polypeptide, R''' is —(CO)—, and —R'''—X is a remainder of the hydrophilic polymer having a functionally reactive moiety when unbound.

3. The pharmaceutical composition of claim 1 wherein the conjugate is formulated as a cream, foam, mousse or spray composition.

4. A method for enhancing keratinocyte growth and migration at an epidermal breach comprising administering to an epidermal breach a therapeutically effective amount of a conjugate comprising a linear hydrophilic polymer covalently bound to a hydrolyzed keratin polypeptide;
wherein the linear hydrophilic polymer is covalently bound to the hydrolyzed keratin polypeptide via the linear hydrophilic polymer having a first end and a second end and the hydrolyzed keratin polypeptide having a functionally reactive moiety, the first end and second end being configured such that when the linear hydrophilic polymer is not covalently bound to the hydrolyzed keratin polypeptide, only the first end is operative to functionally react with the functionally relative moiety to form a covalent bond, and the second end is not operative to functionally react with the functionally relative moiety to form a covalent bond;
wherein the hydrolyzed keratin polypeptide comprises a natural or synthetic functional fragment from a full-length keratin protein;
wherein the functional fragment has a molecular weight from about 45 kDa to about 55 kDa;
wherein the conjugate is not water soluble;
wherein the full length keratin protein is encoded by a gene selected from KRT1, KRT2, KRT3, KRT4, KRT5, KRT6A, KRT6B, KRT6C, KRT7, KRT8, KRT9, KRT10, KRT12, KRT13, KRT14, KRT15, KRT16, KRT17, KRT18, KRT20, KRT23, KRT24, KRT25, KRT26, KRT27, KRT28, KRT71, KRT72, KRT73, KRT74, KRT75, KRT76, KRT77, KRT78, KRT79, KRT80, KRT81, KRT82, KRT83, KRT84, or KRT85; and
wherein the therapeutically effective amount of the conjugate is operative to enhance keratinocyte growth and migration at the epidermal breach.

5. The method of claim 4, wherein the linear hydrophilic polymer without the first end comprises a formula selected from the group consisting of:

Ia

, and

Ib

;

Ic wherein $R_1$ is hydroxyl, carboxy, ethylamine, 2-pyrrolidone, hydroxyethyl methacrylic acid, methylamine, phosphonic acid, sulfonic acid, hydroxyl, or $SO^{4-}$, wherein $R_2$ is hydrogen, methyloxazoline, ethyloxazoline, or propyloxazoline; and wherein n is between 1 and 1,500.

6. The method of claim 4, wherein the linear hydrophilic polymer without the first end has a formula of:

Ia wherein n is between 1 and 1,500.

7. The method of claim 6, wherein n is between about 100 and about 125.

8. The method of claim 6, wherein the linear hydrophilic polymer has a molecular weight of about 5,000 Da.

9. The method of claim 6, wherein the full-length keratin protein has a molecular weight of about 52,000 Da and the hydrophilic polymer has a molecular weight of about 5,000 Da.

10. The method of claim 4, wherein the epidermal breach is dryness, redness or itchiness.

11. The method of claim 4, wherein the epidermal breach is a wound, infection, sore or surgical incision.

12. The method of claim 4, wherein the hydrophilic polymer, when unbound to the hydrolyzed keratin polypeptide, is a mono-functional N-hydroxysuccinimide functionalized polyethylene glycol compound, and wherein the hydrophilic polymer, when unbound to the hydrolyzed keratin polypeptide, has a molecular weight of between about 0.5 and 40 kDa.

13. The method of claim 4, wherein the conjugate is formulated as a spray.

14. The method of claim 4, wherein the conjugate is formulated as a cream.

15. The method of claim 4 wherein the epidermal breach is dermatitis.

16. The method of claim 4 wherein the epidermal breach is an infection, rash, or burn.

17. The method of claim 4 wherein the first end of the linear hydrophilic polymer X, the functionally reactive moiety of the hydrolyzed keratin polypeptide Y, and the conjugate are selected from the group consisting of:

| Hydrolyzed Keratin Polypeptide Y - Functionally Reactive Moiety (Unbound) | Linear Hydrophilic Polymer (X) - Functionally Reactive Moiety (Unbound) | Conjugate |
|---|---|---|
| Y—COOH | HO—X | Y—C(=O)O—X |
| Y—COOH | HS—X | Y—C(=O)S—X |
| Y—SH | (thiol) | Y—S—S—X |
| Y—SH | R'—S—S—X (disulfide) | Y—S—S—X |
| Y—SH | (pyridyl)-S—S—X (dithiopyridyl) | Y—S—S—X |
| Y—NH$_2$ | H(O=)C—X aldehyde | Y—N=CH—X or Y—NH—CH$_2$—X following reduction |
| Y—NH$_2$ | (HO)$_2$HC—X aldehyde hydrate | Y—N=CH—X or Y—NH—CH$_2$—X following reduction |
| Y—NH$_2$ | (R'O)$_2$CH—X or  acetal | Y—N=CH—X or Y—NH—CH—X following reduction |
| Y—NH$_2$ | R'OCH(OH)—X or hemiacetal | Y—N=CH—X or Y—NH—CH—X following reduction |
| Y—NH$_2$ | R'(O=)C—X ketone | Y—N=CR'—X or Y—NH—C(R')H—X following reduction |
| Y—NH$_2$ | (R'O)$_2$C(R')—X or  ketal | Y—N=C(R')—X or Y—NH—C(R')H—X following reduction |
| Y—NH$_2$ | R'OC(R')(OH)—X hemiketal | Y—N=C(R')—X or Y—NH—C(R')H—X following reduction |
| Y—NH$_2$ | R'(S=)C—X ketone thione (thioketone) | Y—N=C(R')—X or Y—NH—C(R')H—X following reduction |
| Y—NH$_2$ | (R'O)(R'S)C(R')—X or  monothioketal | Y—N=C(R')—X or Y—NH—C(R')H—X following reduction |
| Y—NH$_2$ | R'SC(R')(SH)—X or dithiohemiketal | Y—N=C(R')—X or Y—NH—C(R')H—X following reduction |
| Y—NH$_2$ | (R'S)$_2$C(R')—X or  dithioketal | Y—N=C(R')—X or Y—NH—C(R')H—X following reduction |

-continued

| Hydrolyzed Keratin Polypeptide Y - Functionally Reactive Moiety (Unbound) | Linear Hydrophilic Polymer (X) - Functionally Reactive Moiety (Unbound) | Conjugate |
|---|---|---|
| Y—SH<br>Y—OH<br>Y—COOH (anion)<br>Y—NHR" | <br>epoxide (oxirane) | Y—S—$CH_2$—C(OH)(R")—X—<br>Y—O—$CH_2$—C(OH)(R")—X—<br>Y—C(=O)O—$CH_2$—C(OH)(R")—X—<br>Y—NR"—$CH_2$—C(OH)(R")—X— |
| Y—SH<br>Y—OH<br>Y—COOH (anion)<br>Y—NHR" | <br>thioepoxide | Y—S—$CH_2$—C(SH)(R")—X<br>Y—O—$CH_2$—C(SH)(R")—X—<br>Y—C(=O)O—$CH_2$—C(SH)(R")—X—<br>Y—NR"—$CH_2$—C(SH)(R")—X— |
| Y—SH<br>Y—OH<br>Y—NHR"<br>Y—SH<br>Y—OH<br>Y—NHR" | HO—(C=O)—X<br>carboxyl<br>(alcohol)-(C=O)—X<br>carboxylic acid ester<br>(alcohol indicates an esterified suitable alcohol leaving group) | Y—S—(C=O)—X<br>Y—O—(C=O)—X<br>Y—N(R")—(C=O)—X<br>Y—S—(C=O)—X<br>Y—O—(C=O)—X<br>Y—NR"—(C=O)—X |
| Y—$NH_2$ | <br>N-hydroxysuccinimide ester | Y—NH—R'''—X |
| Y—SH | <br>R = H, $CH_3$ | <br>R = H, $CH_3$ |
| Y—$NH_2$ | <br>1-benzotriazole ester | Y—NH—R'''—X |
| Y—$NH_2$<br>Y—(C=NH)—O—(($CH_2$)$_{1-3}$)—$CH_3$<br>(imidoester)<br>Y—COOH<br>Y—(C=O)—R" | $CH_3$—(($CH_2$)$_{1-3}$)—O(C=NH)—X<br>(imidoester)<br>$H_2$N—X<br>$H_2$N—X<br>amine | Y—NH—(C=NH)—X<br>(amidine)<br>Y—(C=NH)—HN—X<br>(amidine)<br>Y—(C=O)—NH—X<br>Y—(R")C=N—X or<br>Y—(R")CH—NH—X following reduction |
| Y—COOH<br>Y—(C=O)—R" | $H_2$N—(C=O)—NH—X<br>urea | Y—(C=O)—NH—(C=O)—NH—X<br>Y—(R")C=N—(C=O)—NH—X or<br>Y—(R")CH—NH—(C=O)—NH—X following reduction |
| Y—COOH<br>Y—(C=O)—R" | $H_2$N—(C=O)—O—X<br>carbamate | Y—(C=O)—NH—(C=O)—O—X<br>Y—(R")C=N—(C=O)—O—X or<br>Y—(R")CH—NH—(C=O)—O—X following reduction |
| Y—COOH<br>Y—(C=O)—R" | $H_2$N—(C=S)—NH—X<br>thiourea | Y—(C=O)—NH—(C=S)—NH—X<br>Y—(R")C=N—(C=S)—NH—X or<br>Y—(R")CH—NH—(C=S)—NH—X following reduction |
| Y—COOH<br>Y—(C=O)—R" | $H_2$N—(C=S)—O—X<br>thiocarbamate | Y—(C=O)—NH—(C=S)—O—X<br>Y—(R")C=N—(C=S)—O—X or<br>Y—(R")CH—NH—(C=S)—O—X following reduction |
| Y—(C=O)—R" | $H_2$N—HN—X | Y—(R")C=N—HN—X<br>hydrazone |

-continued

| Hydrolyzed Keratin Polypeptide Y - Functionally Reactive Moiety (Unbound) | Linear Hydrophilic Polymer (X) - Functionally Reactive Moiety (Unbound) | Conjugate |
|---|---|---|
| Y—NH—NH$_2$ | R''—(O=C)—X | Y—NH—N=C(R'')—X hydrazone |
| Y—NH$_2$ | O=C=N—X isocyanate | Y—NH—(C=O)—NH—X |
| Y—OH | | Y—O—(C=O)—NH—X |
| Y—NH$_2$ | S=C=N—X isothiocyanate | Y—NH—(C=S)—NH—X |
| Y—OH | | Y—O—(C=S)—NH—X |
| Y—SH | H$_2$C=CH—(C=O)—X or H$_2$C=C(CH$_3$)—(C=O)—X alpha-beta unsubstituted carbonyls | Y—S—CH$_2$CH$_2$—(C=O)—X Y—S—CH$_2$—CH(CH$_3$)—(C=O)—X |
| Y—SH | H$_2$C=CH—(C=O)O—X alpha-beta unsubstituted carboxyl | Y—S—CH$_2$CH$_2$—(C=O)O—X |
| Y—SH | H$_2$C=C(CH$_3$)—(C=O)—O—X alpha-beta unsubstituted carboxyls (methacrylates) | Y—S—CH$_2$CH(CH$_3$)—(C=O)O—X |
| Y—SH | H$_2$C=CH—(C=O)NH—X alpha-beta unsubstituted amides (acrylamides) | Y—S—CH$_2$CH$_2$—(C=O)NH—X |
| Y—SH | vinyl pyridine-X (2- or 4-vinylpyridine) | Y—S—CH$_2$—CH$_2$-(pyridyl)-X |
| Y—SH | H$_2$C=CH—SO$_2$—X (vinyl sulfone) | Y—S—H$_2$C—CH$_2$—SO$_2$—X |
| Y—SH | ClH$_2$C—CH$_2$—SO$_2$—L (chloroethyl sulfone) | Y—S—H$_2$C—CH$_2$—SO$_2$—X |
| Y—SH | (halogen)-CH$_2$—(C=O)—O—X (halogen)-CH$_2$—(C=O)—NH—X (halogen)-CH$_2$—(C=O)—X | Y—S—CH$_2$—(C=O)—O—X Y—S—CH$_2$—(C=O)—NH—X Y—S—CH$_2$—(C=O)—X |
| Y—O(C=O)—CH$_2$-(halogen) Y—NH(C=O)—CH$_2$-(halogen) Y—(C=O)—CH$_2$-(halogen) | HS—X | Y—O(C=O)—CH$_2$—S—X Y—NH(C=O)—CH$_2$—S—X Y—(C=O)—CH$_2$—S—X |
| Y—SH | (halogen)-CH$_2$(C=O)O—X (halogen)-CH$_2$(C=O)NH—X (halogen)-CH$_2$(C=O)—X | Y—S—CH$_2$(C=O)O—X Y—S—CH$_2$(C=O)NH—X Y—S—CH$_2$(C=O)—X |
| Y—N$_3$ | HC≡C—X | triazole: Y—N linked to ring with N=N and X substituent |
| Y—N$_3$ | 2-(diphenylphosphino)phenyl carbonate with X (Ph$_2$P—C$_6$H$_4$—O—C(=O)—X) | Y—NH—C(=O)—X |
| Y—N$_3$ | Ph$_2$P—CH$_2$—S—C(=O)—X | Y—NH—C(=O)—X |
| Y—SH | aziridine-X (HN—CH$_2$—CH(X) ring) | Y—S—CH$_2$—CH(NH$_2$)—X |
| Y—NH$_2$ | (F$_5$—Ph)—OC(O)—X | Y—NH—C(O)—X | wherein R' is $C_{1-6}$ alkyl, $C_{3-6}$ cycloalkyl, or an aryl group having 5-8 endocyclic atoms;

wherein R" is H, $C_{1-6}$ alkyl, $C_{3-6}$ cycloalkyl, or an aryl group having 5-8 endocyclic atoms; and wherein R' is $C_{1-6}$ alkyl, $C_{3-6}$ cycloalkyl, or an aryl group having 5-8 endocyclic atoms;

wherein R" is H, $C_{1-6}$ alkyl, $C_{3-6}$ cycloalkyl, or an aryl group having 5-8 endocyclic atoms; and wherein R''' is a carbonyl derivative *—(C=O)—, *—(C=O)—(CH$_2$)$_{1-8}$—, *—(C=O)—(CH$_2$)$_{1-8}$—S—S—, *—(C=O)—(CH$_2$)$_{1-8}$—(C=O)—O—, *—(C=O)—(CH$_2$)$_{1-8}$—O—(C=O)—, *—(C=O)—(CH$_2$)$_{1-8}$—(C=O)—NH—, or *—(C=O)—(CH$_2$)$_{1-8}$—NH—(C=O)—, or alternatively, R''' is a carbonyl derivative of the form *—(C=O)—O—(CH$_2$)$_{1-8}$—S—S—, *—(C=O)—O—(CH$_2$)$_{1-8}$—(C=O)—O—, *—(C=O)—O—(CH$_2$)$_{1-8}$—(C=O)—O—(CH$_2$)$_{1-8}$—*—(C=O)—O—(CH$_2$)$_{1-8}$—O—(C=O)—, *—(C=O)—O—(CH$_2$)$_{1-8}$—(C=O)—NH—, or *—(C=O)—O—(CH$_2$)$_{1-8}$—NH—(C=O)—, where "*" indicates the point of attachment to succinimidyl or benzotriazolyl groups.

\* \* \* \* \*